United States Patent
Kim et al.

(10) Patent No.: US 8,140,146 B2
(45) Date of Patent: Mar. 20, 2012

(54) CATHETER TIP DEVICE AND METHOD FOR MANUFACTURING SAME

(75) Inventors: Woojin Kim, Livermore, CA (US); Michael Klitzke, Fremont, CA (US); Mark Sheward, San Ramon, CA (US); Brad Jeffrey Neiman, San Francisco, CA (US)

(73) Assignee: General Electric Company, Schenectady, NY (US)

(*) Notice: Subject to any disclaimer, the term of this patent is extended or adjusted under 35 U.S.C. 154(b) by 887 days.

(21) Appl. No.: 12/130,539

(22) Filed: May 30, 2008

(65) Prior Publication Data

US 2009/0299178 A1 Dec. 3, 2009

(51) Int. Cl.
*A61M 25/01* (2006.01)
(52) U.S. Cl. ........ 600/435; 600/488; 600/561; 600/486; 604/264
(58) Field of Classification Search .......... 600/300–301, 600/372–397, 433–435, 466, 485, 585; 604/508, 604/96.01, 264, 523, 528, 544, 349, 915, 604/919, 921; 607/122
See application file for complete search history.

(56) References Cited

U.S. PATENT DOCUMENTS

| | | | |
|---|---|---|---|
| 3,748,623 A | 7/1973 | Millar | |
| 4,274,423 A | 6/1981 | Mizuno et al. | |
| 4,722,348 A * | 2/1988 | Ligtenberg et al. | 600/488 |
| 4,901,731 A | 2/1990 | Millar | |
| 5,050,297 A * | 9/1991 | Metzger | 600/488 |
| 5,836,886 A * | 11/1998 | Itoigawa et al. | 600/488 |
| 5,902,248 A * | 5/1999 | Millar et al. | 600/485 |
| 5,951,487 A * | 9/1999 | Brehmeier-Flick et al. | 600/561 |
| 6,019,729 A * | 2/2000 | Itoigawa et al. | 600/485 |
| 6,394,986 B1 | 5/2002 | Millar | |
| 6,974,422 B1 | 12/2005 | Millar | |
| 6,994,695 B1 | 2/2006 | Millar | |
| 2001/0056280 A1 | 12/2001 | Underwood et al. | |

(Continued)

FOREIGN PATENT DOCUMENTS

EP 0115548 A 8/1984

(Continued)

OTHER PUBLICATIONS

Yuan, T.D. "Convection Modeling of Flip chip and Wirebond Surface Mounted Modules", IEEE Intersociety Conference on Thermal Phenomenon, 1996, p. 174-179.*

(Continued)

*Primary Examiner* — Henry M Johnson, III
*Assistant Examiner* — Marie Archer
(74) *Attorney, Agent, or Firm* — GE Global Patent Operation; Mark A. Conklin

(57) ABSTRACT

A catheter tip device and methods for manufacturing a catheter tip device are disclosed, the device comprising a transducer module attached to a capsule, wherein the transducer module comprises a carrier including a recessed die-attach area, a transducer die located in the recessed die-attach area, and at least one conductive lead deposited onto the carrier and interconnected to the transducer die. The recessed die-attach area has an outer perimeter greater than the outer perimeter of the transducer die forming a groove between at least one edge of the transducer die and the outer perimeter in which an adhesive agent is located to attach the transducer die to the recessed die-attach area. The methods of manufacturing the catheter tip device involve the use of an array of carriers.

19 Claims, 6 Drawing Sheets

U.S. PATENT DOCUMENTS

2007/0118035 A1    5/2007   Secora

FOREIGN PATENT DOCUMENTS

| EP | 0419294 A | 3/1991 |
| WO | WO 9006723 A1 * | 6/1990 |
| WO | 97/21381 A2 | 6/1997 |
| WO | 2008/014310 A2 | 1/2008 |

OTHER PUBLICATIONS

Butler, J. T. et al. "Multichip module packaging of microelectromechanical systems", Sensors and Actuators A70 (1998), 15-22.*

Esashi, M. et al "Fabrication of Catheter-Tip and Sidewall Miniature Pressure Sensors", IEEE Transactions on Electron Devices, vol. ED. 29, No. 1, Jan. 1989, p. 57-63.*

Gilleo, K. et al in the ECWC 10 Conference at IPC Printed Circuits Expo®, SMEMA Council APEX® and Designers Summit 05, p. S01-3-1 to S01-3-14.*

Gilleo, K et al in "Injection Molded and Microfabrication electronic packaging", Matrix Inc., Molding 2005, p. 1-14.*

Li, C. et al in "Polymer flip-chip bonding of pressure sensors on a flexible Kapton film for neonatal catheters", J. Micromech. Microeng. 15 (2005) 1729-1735.*

Khanna, P.K. et al in "Miniature pressure sensor and micromachined actuator structure based on low-temperature-cofired ceramics and piezoelectric material", Materials Chemistry and Physics 87 (2004) 173-178.*

PCT International Application No. PCT/US2009/040345: Written Opinion and International Search Report, completed Jun. 22, 2009.

* cited by examiner

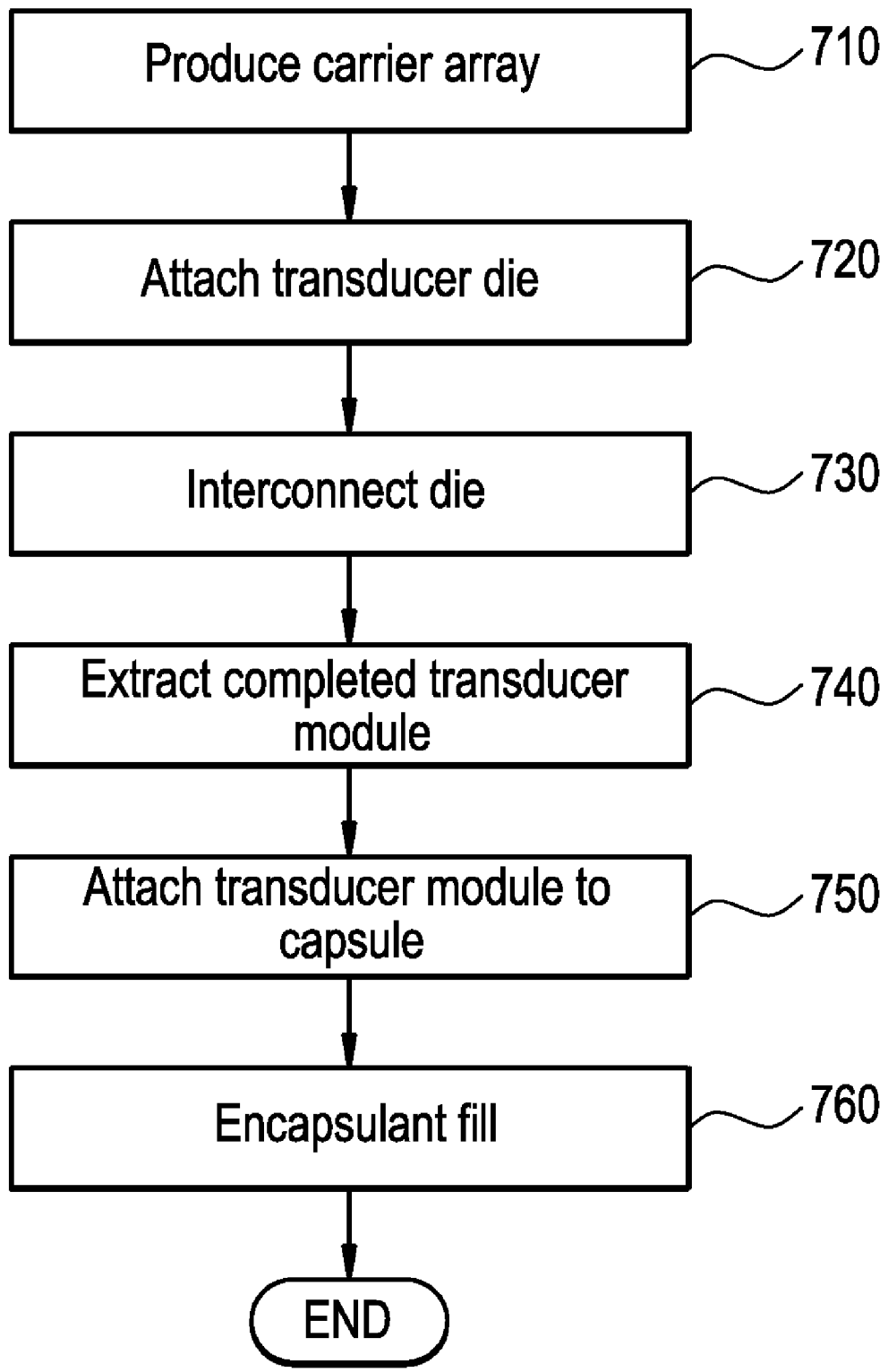

CATHETER TIP DEVICE AND METHOD FOR MANUFACTURING SAME

BACKGROUND OF THE INVENTION

This invention relates generally to catheters, and more particularly to a catheter tip device.

Catheter tip devices are widely used in the medical diagnostics field for carrying various devices, including integrated circuit die, mounted in the catheter tip. In one example, a sensor die within a catheter tip is insertable into a living body through a body orifice or a surgical incision. The components and construction of these existing catheter tip devices require that several steps of the manufacturing and assembly process be performed manually, including die attachment and wire attachment for electrical connections. Placement of a die onto a flat carrier surface is often difficult or inaccurate. In addition, perimeter sealing of the die attached to a flat carrier surface often results in overflow of the adhesive agent used to make the attachment. In order to decrease the manufacturing costs and human error associated with such manufacture, it would be advantageous to provide a catheter tip device that does not require that several steps of the manufacturing and assembly process be performed manually.

BRIEF DESCRIPTION OF THE INVENTION

A catheter tip device and methods for manufacturing of a catheter tip device are disclosed, the device comprising a transducer module attached to a capsule, wherein the transducer module comprises a carrier including a recessed die-attach area, a transducer die located in the recessed die-attach area, and at least one conductive lead deposited onto the carrier and interconnected to the transducer die. The recessed die-attach area has an outer perimeter greater than the outer perimeter of the transducer die forming a groove between at least one edge of the transducer die and the outer perimeter in which an adhesive agent is located to attach the transducer die to the recessed die-attach area. The methods of manufacturing the catheter tip device involve the use of an array of carriers.

BRIEF DESCRIPTION OF THE DRAWINGS

FIG. 7 illustrates a flowchart of an alternate embodiment of a method for manufacturing a catheter tip device.

DETAILED DESCRIPTION OF THE INVENTION

Figure 1:
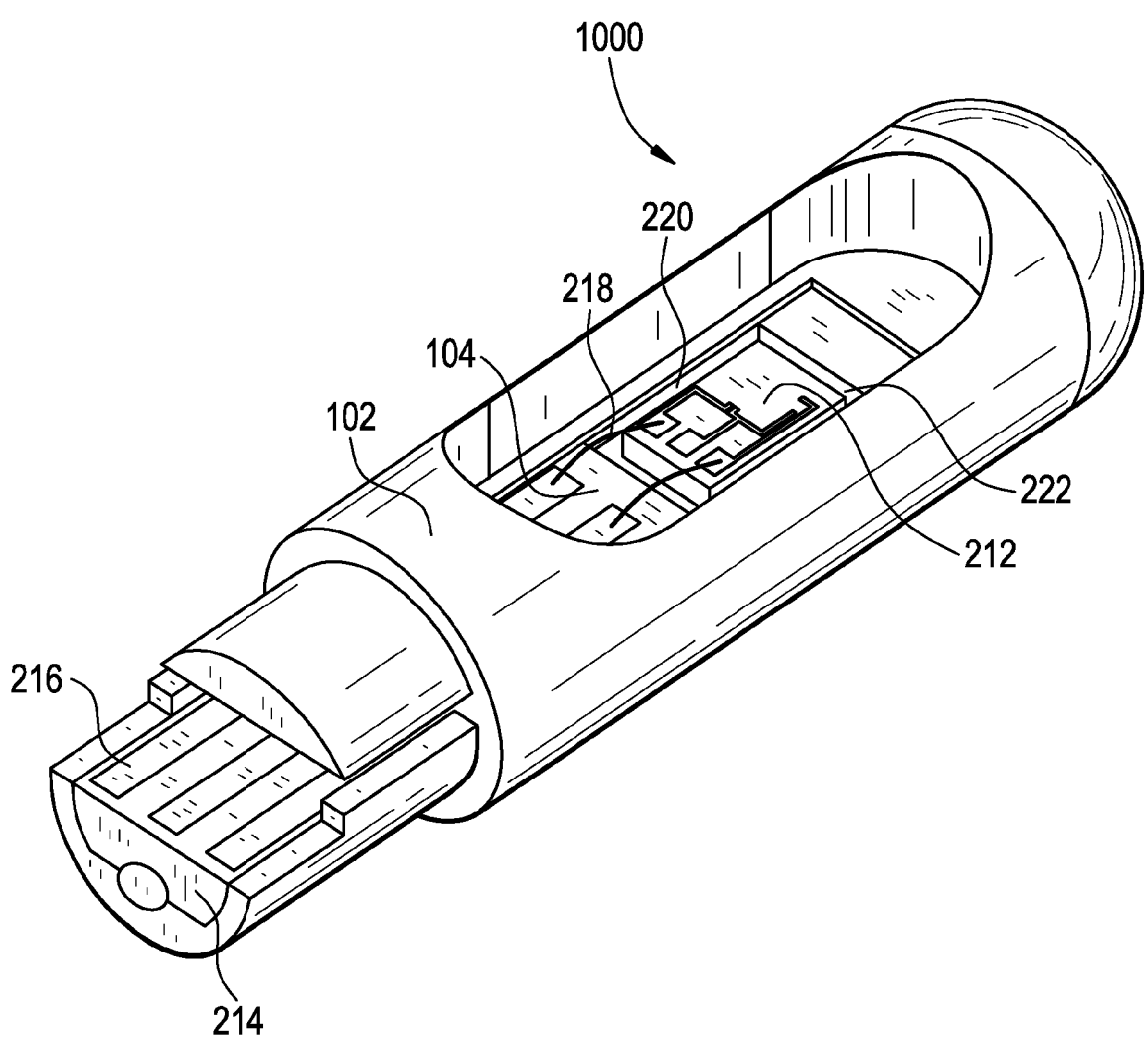
FIG. 1 illustrates a perspective view of a catheter tip device according to one embodiment of the invention.
Figure 2:
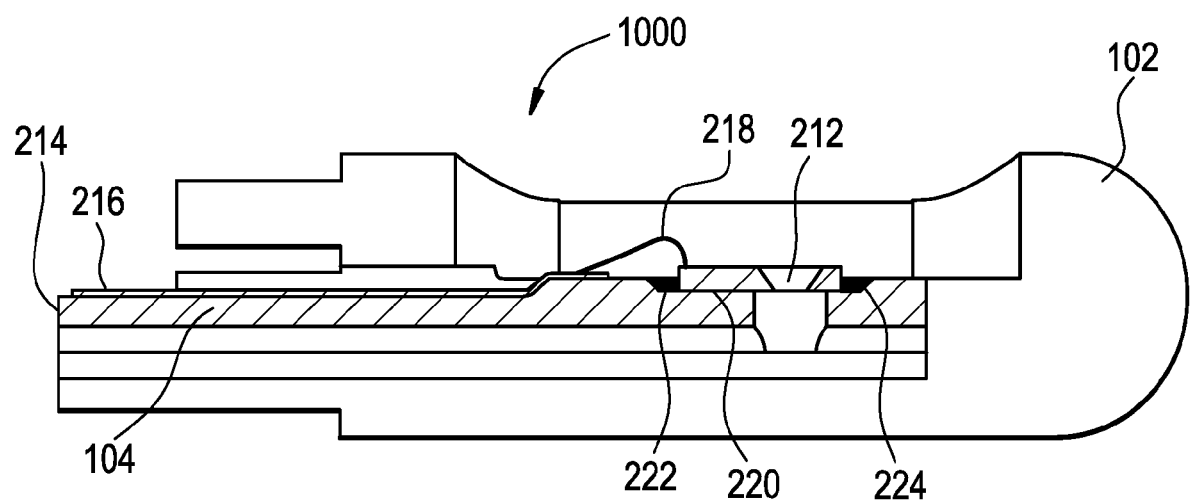
FIG. 2 illustrates a cross-section view of a catheter tip device according to one embodiment of the invention.

There is provided a catheter tip device 1000 for carrying one or more integrated circuit die 212 mounted in the catheter tip, including, for example, die for transducers (e.g., sensors and actuators), data processing devices (e.g., ASIC microprocessors), and telemetric devices (e.g., for wireless or RF communication), that can be configured to provide an electrical signal output in response to an external boundary condition (e.g., pressure, temperature, pH, etc.). The catheter tip device 1000 can be insertable into a living body through a body orifice or a surgical incision and can be used for a variety of applications, including, for example, to perform direct measurement within the body of pressure, temperature, pH, etc. In one embodiment of the invention, shown in FIGS. 1 and 2, the catheter tip device 1000 can comprise a transducer module 104 attached to a capsule 102.

In one aspect of the invention, the capsule 102 can be made of a bio-compatible material, e.g., a plastic material. In one embodiment of the invention, the capsule 102 material can be an ISO 10993-compliant material. A skilled artisan would appreciate the fact that other medical-grade materials can be within the scope and the spirit of the invention, including, for example, metal, ceramic, or composite materials. In another aspect of the invention, the capsule 102 can have a substantially cylindrical form factor, with a window configured to at least partially expose the transducer module 104. A skilled artisan would appreciate the fact that other form factors of the capsule 102 can be within the scope and the spirit of the invention.

Figure 3:
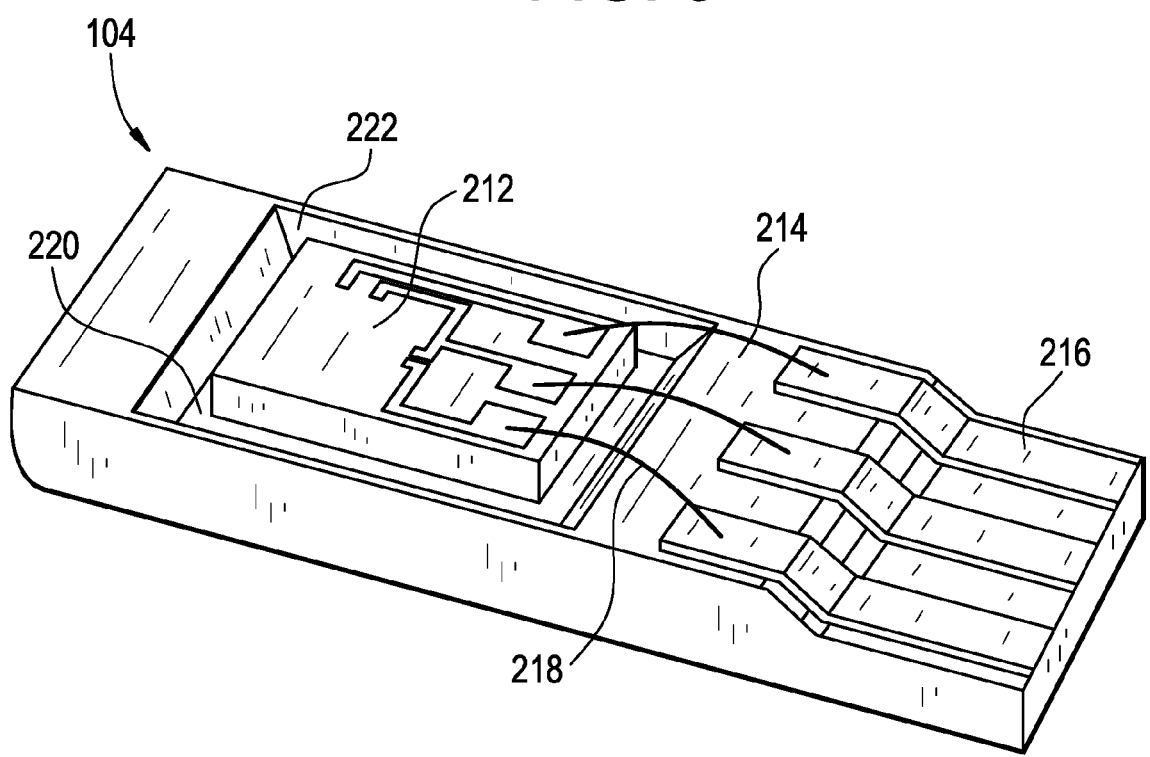
FIG. 3 illustrates a perspective view of a transducer module in one embodiment of the invention.

In a further aspect of the invention, the transducer module 104 can include at least one transducer die 212 attached to a carrier 214, best viewed in FIG. 3. The transducer die 212 can be, for example, a micro-machined sensing or actuator element. The carrier 214 can be manufactured using molded interconnect device (MID) technology. In one embodiment of the invention, the carrier 214 can be made of a plastic material. In another embodiment of the invention, the carrier 214 can be made of a ceramic material. A skilled artisan would appreciate the fact that other materials for manufacturing the carrier 214 can be within the spirit and the scope of the present invention.

In a further aspect of the invention, one or more conductive leads 216 can be deposited onto the carrier 214, e.g., by metal plating, as a substitute for a conventional printed circuit board. The conductive leads 216 can be used for interconnecting the transducer die 212 to a device equipped to receive the electrical signals from the transducer die 212. These conductive leads 216 are typically metallic.

In a further aspect of the invention, the carrier 214 can have a recessed die-attach area 220 (or well) whose outer perimeter is greater than the outer perimeter of the transducer die 212 received within the recessed die-attach area 220, thereby forming an open groove 222 between one or more edges of the transducer die 212 and the outer perimeter of the recessed die-attach area 220 when the transducer die 212 is placed into the recessed die-attach area 220. The recessed die-attach area 220 can facilitate the placing of the transducer die 212 onto the carrier 214. In another embodiment of the invention, the recessed die-attach area 220 can receive a transducer die 212 and another die device (e.g., ASIC, RF transceiver, etc.). In yet another embodiment of the invention, the carrier 214 can include two or more recessed die-attach areas 220 for individually receiving two or more die.

In another aspect of the invention, the transducer die 212 can be attached to the recessed die-attach area 220 using an adhesive agent 224, such as a silicone gel or a Room Temperature Vulcanized (RTV) silicone, in the groove 222 formed between the edges of the transducer die 212 and the outer perimeter of the recessed die-attach area 220. The groove 222 prevents overflow of the adhesive agent 224.

In another aspect of the invention, the transducer die 212 can be interconnected to one or more conductive leads 216. In one embodiment of the invention, the interconnect 218 between the transducer die 212 and the conductive leads 216 can be an electrical interconnect provided by one or more bond wires. The bond wires can be provided by fine wires having a diameter of, e.g., 25 μm to 75 μm. The bond wires can be made, e.g., of gold, aluminum, silver, or copper. A skilled artisan would appreciate the fact that other wire materials can be within the scope and the spirit of the present invention. In another embodiment of the invention, the electrical interconnect of the transducer die 212 to the conductive leads 216 can be provided by using flip-chip technology using solder bumps instead of bond wires.

In another aspect of the invention, the transducer module 104 can be attached to the capsule 102 in a variety of ways, including, e.g., plastic welding, solvent bonding, or using an adhesive agent. The capsule 102 can be filled with an encapsulant (not shown) provided, e.g., by a dielectric silicone potting.

Figure 4:
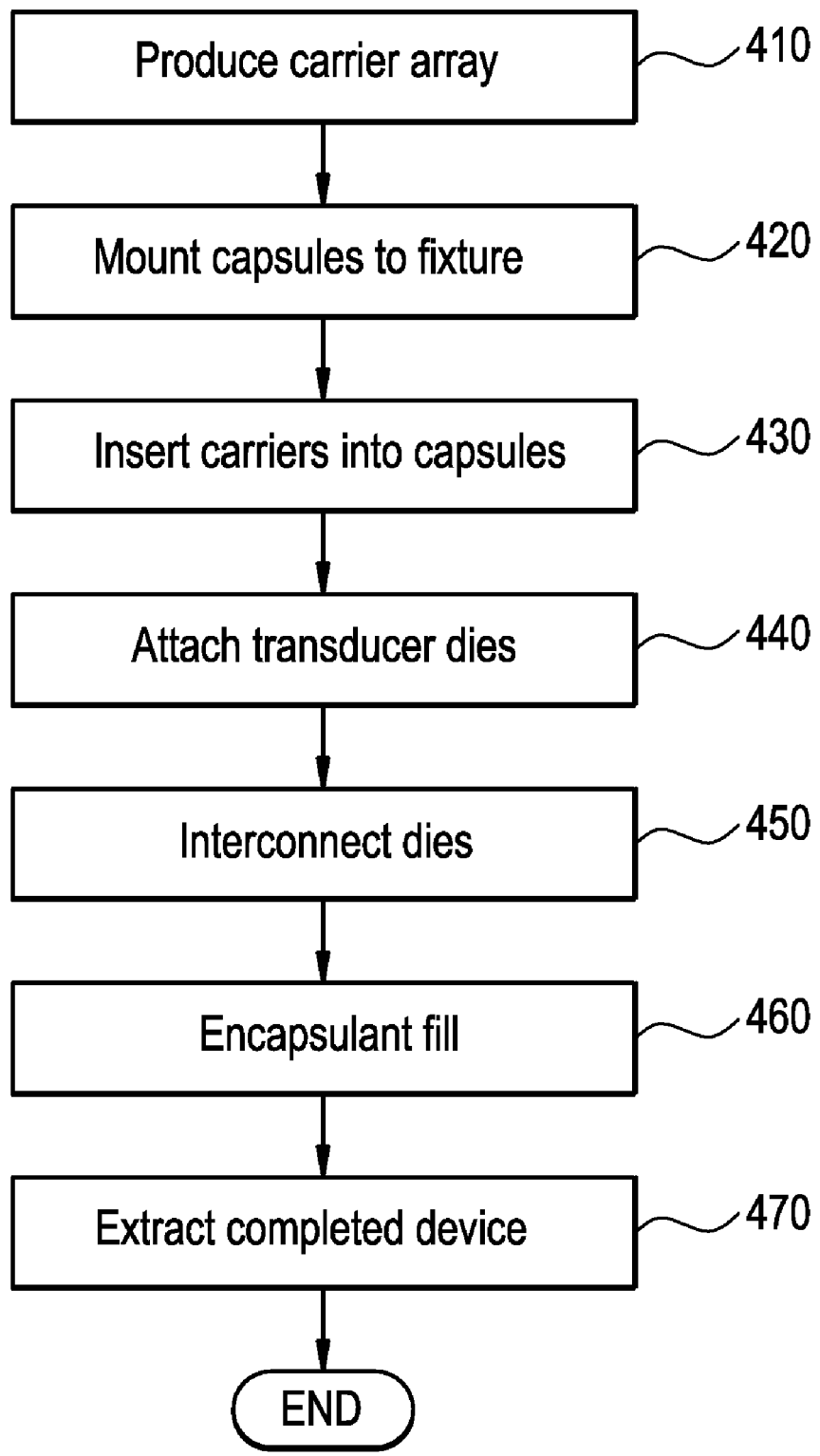
FIG. 4 illustrates a flowchart of one embodiment of a method for manufacturing a catheter tip device.

One embodiment of a method for manufacturing a catheter tip device 1000 is now being described with references to the flowchart shown in FIG. 4. In this embodiment of the invention, several steps of the manufacturing process can be fully automated thus providing for significant quality improvement and cost reduction.

Figure 5:
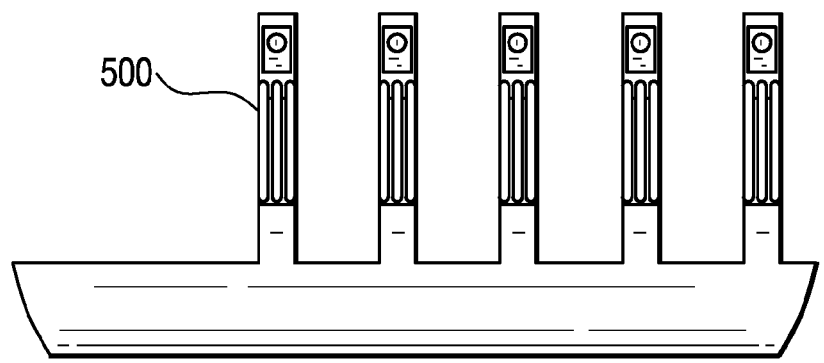
FIG. 5 illustrates an array of carriers in one embodiment of the invention.

At step 410, an array 500 (best viewed in FIG. 5) of carriers 214 can be produced using MID technology. The carriers 214 can have conductive leads 216 incorporated. Each carrier 214 can have at least one recessed die-attach area 220 as shown in FIG. 3 for attaching at least one transducer die 212. This step 410 can be performed by an automated process.

Figure 6:
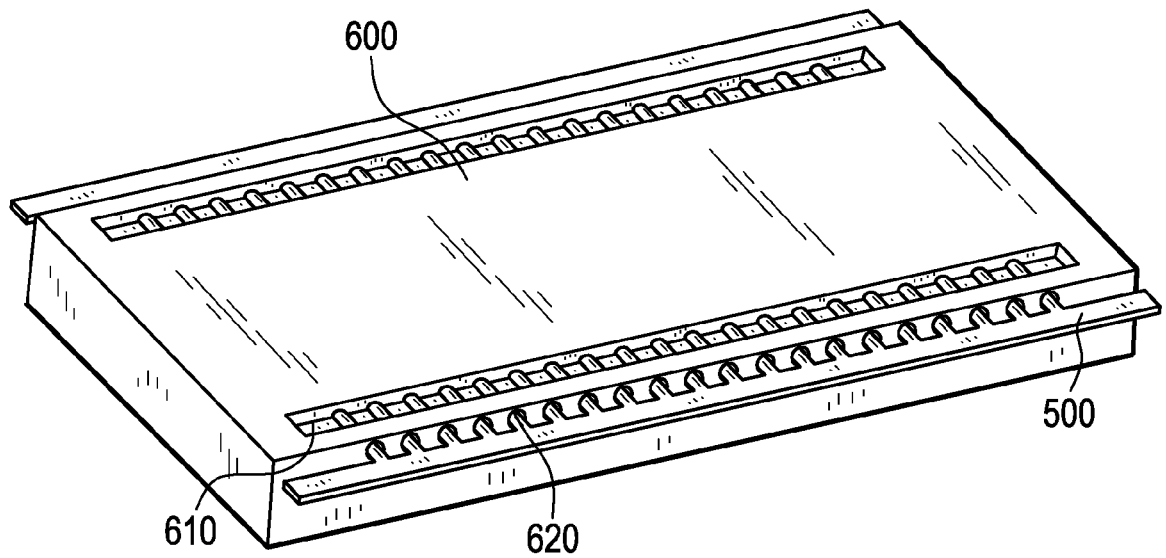
FIG. 6 illustrates a fixture for mounting a plurality of capsules and an array of carriers during manufacturing in one embodiment of the invention.

At step 420, a plurality of capsules 102 can be mounted to a fixture 600 (best viewed in FIG. 6). The fixture 600 can have at least one recessed area 610 with openings 620 configured to receive the capsules 102. In one aspect of the invention, a mechanism would be provided to hold each of the capsules 102 in place within the fixture 600 at the same orientation. In one embodiment of the invention, the capsules 102 can be provided in an array to facilitate placement into the openings 620 of the fixture 600. This step 420 can be performed by an automated process.

At step 430, the carriers 214 comprising the array 500 can be inserted into and attached to the capsules 102 mounted in the fixture 600. This step 430 can be performed by an automated process.

At step 440, at least one transducer die 212 can be picked-and-placed into the recessed die-attach area 220 of each carrier 214 of the array 500. The transducer die 212 can be attached to the recessed die-attach area 220 using an adhesive agent 224, such as a silicone gel or a Room Temperature Vulcanized (RTV) silicone, in the groove 222 formed between the edges of the transducer die 212 and the outer perimeter of the recessed die-attach area 220. This recessed die-attach area 220 and groove 222 also allows for the use of B-stage epoxy by placing the pre-formed epoxy in the recessed die-attach area 220, then placing the transducer die 212, and then reflowing the epoxy without the risk of overflow. This step can be performed by an automated process.

At step 450, each transducer die 212 can be interconnected to one or more conductive leads 216 of the respective carrier 214 of the array of carriers 214. In one embodiment of the invention, the interconnect 218 between the transducer die 212 and the conductive leads 216 can be provided by one or more bond wires. The bond wires can be attached to the die 212 and to the conductive leads 216 by, e.g., wedge bonding or ball bonding using, e.g., thermocompression or thermoscopic bonding methods. This step can be performed by an automated process. In another embodiment of the invention, the interconnecting of the transducer die 212 to the conductive leads 216 can be provided by using flip-chip technology, using solder bumps instead of bond wires. The solder bumps can be deposited on the transducer die 212, and the interconnecting can be achieved by flipping the transducer die 212 around so that the top side would face a mounting area where the solder bumps can be connected directly to the conductive leads 216. This step can be performed by an automated process. A skilled artisan would appreciate the fact that other methods of providing the interconnect of the transducer die 212 to the conductive leads 216 can be within the scope and the spirit of the present invention.

Upon completion of step 450, an array comprising a plurality of completed transducer modules 104 can be produced, each transducer module 104 in the array comprising a transducer die 212 attached to a carrier 214, and one or more interconnects 218 between the transducer die 212 and the conductive leads 216 of the carrier 214.

At step 450, the capsules 102 can be filled with an encapsulant provided, e.g., by a dielectric silicone potting by an automated process to protect the transducer die 212 and interconnect 218 from the external environment.

At step 470, a completed transducer module 104 can be extracted from the array of carriers 214. This step can be performed by an automated process.

Another embodiment of a method for manufacturing a catheter tip device 1000 is now being described with references to the flowchart shown in FIG. 7. In this embodiment of the invention, several steps of the manufacturing process can be fully automated thus providing for significant quality improvement and cost reduction.

At step 710, an array of carriers 214 can be produced using MID technology. The carriers 214 can have conductive leads 216 incorporated. Each carrier 214 can have at least one recessed die-attach area 220 as shown in FIG. 3 for attaching at least one transducer die 212. This step can be performed by an automated process.

At step 720, at least one transducer die 212 can be attached to each carrier 214 of the array of carriers 214, e.g., using an adhesive agent 224. In one embodiment, the transducer die 212 can be attached to at least one recessed die-attach area 220, wherein a groove 222 is formed between at least one edge of the transducer die 212 and the outer perimeter of the recessed die-attach area 220 as shown in FIG. 3. This step can be performed by an automated process.

At step 730, interconnects 218 between the transducer die 212 and one or more conductive leads 216 of the respective carrier 214 of the array of carriers 214 can be provided using bond wires or flip-chip technology.

Upon completion of step 730, an array comprising a plurality of completed transducer modules 104 can be produced, each transducer module 104 of the array comprising a transducer die 212 attached to a carrier 214, and one or more interconnects 218 between the transducer die 212 and the conductive leads 216 of the carrier 214.

At step 740, a completed transducer module 104 can be extracted from the array of carriers 214. This step can be performed by an automated process.

At step 750, the complete transducer module 104 can be attached to a capsule 102, e.g., via plastic welding, solvent bonding, or using an adhesive agent, by a manual or an automated process.

At step 760, the capsule 102 can be filled with an encapsulant provided, e.g., by a dielectric silicone potting by an automated process to protect the transducer die 212 and interconnect 218 from the external environment. Upon completion of step 760, a catheter tip device 1000 is produced.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A catheter tip device comprising:
   a capsule having a window;
   a transducer module attached to said capsule, said transducer module comprising,
   a carrier comprising molded plastic, wherein the carrier has a first end on the inside of the capsule and a second end extending outside of the capsule, the carrier including a recessed die-attach area at the first end of the carrier at least partially exposed by the window,
   a transducer die located in said recessed die-attach area,
   at least one conductive lead deposited onto said carrier, and
   at least one wirebond coupling the transducer die to the at least one conductive lead,
   wherein the at least one conductive lead has a first end proximate the recessed die-attach area and a second end at the second end of the carrier extending outside of the capsule,
   wherein said recessed die-attach area has an outer perimeter that forms a groove with at least one edge of said transducer die, and
   wherein an adhesive agent is located in said groove to attach said transducer die to said recessed die-attach area.

2. The catheter tip device of claim 1, wherein said at least one conductive lead is electrically interconnected to said transducer die using flip chip technology.

3. The device of claim 1, wherein said capsule has a substantially cylindrical form.

4. The catheter tip device of claim 1, wherein said transducer die is a sensor.

5. The catheter tip device of claim 1, wherein said transducer die is an actuator.

6. A method for manufacturing catheter tip devices, said method comprising the steps of:
   producing an array of carriers, each of said carrier comprising molded plastic and including a recessed die-attach area and at least one conductive lead deposited onto said carrier;
   mounting a plurality of capsules to a fixture, each of said capsules having a Window;
   inserting said array of carriers into said plurality of capsules mounted to said fixture;
   attaching at least one transducer die to said recessed die-attach area of each of said carrier; and
   interconnecting said at least one transducer die to said at least one conductive lead of each of said carrier,
   wherein the carrier has a first end on the inside of the capsule and a second end extending outside of the capsule, and wherein the recessed die-attach area is at least partially exposed by the window, and
   wherein the at least one conductive lead has a first end proximate the recessed die-attach area and a second end at the second end of the carrier extending outside of the capsule.

7. The method of claim 6, wherein said step of attaching at least one transducer die to said recessed die-attach area of each said carrier comprises the steps of:
   placing said transducer die in said recessed die-attach area of to form a groove between at least one edge of said transducer die and the outer perimeter of said recessed die-attach area; and
   providing an adhesive agent located in said groove.

8. The method of claim 6, wherein said interconnecting of said at least one transducer die to said at least one conductive lead is provided by at least one bond wire.

9. The method of claim 6, wherein said interconnecting of said at least one transducer die to said at least one conductive lead is provided by using flip chip technology.

10. A method for manufacturing a catheter tip device, said method comprising the steps of:
    producing an array of carriers, each of said carrier comprising molded plastic and including a recessed die-attach area and at least one conductive lead deposited onto said carrier;
    attaching at least one transducer die to said recessed die-attach area of each of said carrier;
    forming an array of transducer modules by interconnecting said at least one transducer die to said at least one conductive lead of each of said carrier;
    separating said transducer modules from the array; and
    attaching one of said transducer modules to a capsule having a window,
    wherein each of said carrier has a first end on the inside of the capsule and a second end extending outside of the capsule, and wherein the recessed die-attach area is at least partially exposed by the window, and
    wherein the at least one conductive lead has a first end proximate the recessed die-attach area and a second end at the second end of the carrier extending outside of the capsule.

11. The method of claim 10, wherein said step of attaching at least one transducer die to said recessed die-attach area of each said carrier comprises the steps of:
    placing said transducer die in said recessed die-attach area to form a groove between at least one edge of said transducer die and the outer perimeter of said recessed die-attach area; and
    providing an adhesive agent located in said groove.

12. The method of claim 10, wherein said interconnecting of said at least one transducer die to said at least one conductive lead is provided by at least one bond wire.

13. The method of claim 10, wherein said interconnecting of said at least one transducer die to said at least one conductive lead is provided by using flip chip technology.

14. The method of claim 10, wherein said step of attaching said transducer module to said capsule is performed by a process selected from the group consisting of welding, solvent bonding, using an adhesive agent, or combinations thereof.

15. The catheter tip device of claim 1, wherein the adhesive agent comprises a silicone gel.

16. The catheter tip device of claim 1, wherein the adhesive agent comprises a room temperature vulcanized (RTV) silicone.

17. The catheter tip device of claim 1, further comprising an encapsulant disposed in the capsule.

18. The catheter tip device of claim 17, wherein the encapsulant comprises a dielectric silicone potting.

19. The catheter tip device of claim 1, wherein the capsule comprises a bio-compatible material.

* * * * *